United States Patent
Aqeel (12)

(10) Patent No.: US 10,987,470 B2
(45) Date of Patent: Apr. 27, 2021

(54) SYRINGE WITH PLUNGER EXTENSION

(71) Applicant: William A. Aqeel, Yonkers, NY (US)

(72) Inventor: William A. Aqeel, Yonkers, NY (US)

(73) Assignee: William A. Aqeel, Yonkers, NY (US)

( * ) Notice: Subject to any disclaimer, the term of this patent is extended or adjusted under 35 U.S.C. 154(b) by 111 days.

(21) Appl. No.: 16/294,692

(22) Filed: Mar. 6, 2019

(65) Prior Publication Data

US 2019/0275258 A1  Sep. 12, 2019

Related U.S. Application Data

(60) Provisional application No. 62/639,827, filed on Mar. 7, 2018.

(51) Int. Cl.
| | | |
|---|---|---|
| *A61M 5/315* | (2006.01) | |
| *A61M 5/145* | (2006.01) | |
| *A61M 5/32* | (2006.01) | |

(52) U.S. Cl.
CPC .... *A61M 5/31513* (2013.01); *A61M 5/31505* (2013.01); *A61M 5/1458* (2013.01); *A61M 5/322* (2013.01)

(58) Field of Classification Search
CPC .............. A61M 5/1458; A61M 5/322; A61M 5/31511; A61M 5/5066; A61M 5/315; A61M 5/31565; A61M 5/31566; A61M 5/31576; A61M 5/31578; A61M 5/3148
See application file for complete search history.

(56) References Cited

U.S. PATENT DOCUMENTS

| | | | | |
|---|---|---|---|---|
| 3,325,061 | A * | 6/1967 | Ellsworth | A61M 5/3137 222/386 |
| 4,464,174 | A * | 8/1984 | Ennis | A61M 5/284 604/236 |
| 4,639,248 | A * | 1/1987 | Schweblin | A61B 10/0045 422/923 |
| 6,458,095 | B1 * | 10/2002 | Wirt | A61B 17/00491 222/137 |
| 9,302,052 | B1 * | 4/2016 | Rafaat | A61M 5/31591 |
| 2013/0131606 | A1 * | 5/2013 | Bertocci | A61M 5/315 604/221 |
| 2013/0197451 | A1 * | 8/2013 | Ishii | B32B 27/00 604/221 |
| 2013/0331817 | A1 * | 12/2013 | Woehr | A61M 5/31 604/506 |

* cited by examiner

*Primary Examiner* — Bhisma Mehta
*Assistant Examiner* — Robert F Allen
(74) *Attorney, Agent, or Firm* — Limin Wen

(57) ABSTRACT

A single-hand controlled syringe with plunger extension includes a barrel, a plunger fit to the barrel, and a plunger extension integrated with the plunger. The plunger extension consists of a head, a back, and a body between the head and the back. The body of the plunger extension is oriented parallel to the plunger, with integrated connection at the back of the plunger extension and the back of the plunger. Depressing the head of the plunger extension moves the syringe from the contracted state to the retracted state. Such syringe with plunger extension is useful to draw blood or fluid with a single hand.

1 Claim, 2 Drawing Sheets

SYRINGE WITH PLUNGER EXTENSION

REFERENCE TO RELATED APPLICATION

This application claims the benefit of the filing date of US Provisional Patent Application Ser. No. 62/639,827 filed on Mar. 7, 2018, entitled "IMPROVED SYRINGE WITH PLUNGER EXTENSION". The teachings of the entire referenced application is incorporated herein by reference.

FIELD OF THE INVENTION

The present invention relates generally to medical and veterinary devices, and more particularly to syringes.

BACKGROUND OF THE INVENTION

Blood and bodily fluid draws are in theory a simple medical procedure: stick the patient with a needle, advance the tip of the needle to a targeted location, draw the blood or other bodily fluid through the needle into a syringe or reservoir, and retract the needle. These procedures should be quick and relatively easy.

Add a live patient and that theoretical ideal falls away. While some adult humans can give blood easily, many are squeamish. Babies are unaware of what is about to happen until they are pricked, at which point they thrash and scream. Child patients squirm and cry before and during the procedure, doing their best to avoid the needle. Animals are an entirely different category, and the difficulty of drawing blood from a small animal, such as a dog, or a large animal, such as a horse, cannot be overestimated. A "simple" blood or fluid draw is quite a challenging practice for veterinarians.

When an assistant is available, drawing a fluid may be performed while the assistant holds the patient steady and the worker uses two hands to hold the syringe and retract the plunger. But often there is no assistant, and the health worker needs to perform the draw on his own. With larger animals, regardless of the presence of an assistant, the health worker may need to use one hand to stabilize the animal at the draw location and, with the other hand, both hold the syringe and retract the plunger.

When faced with having to perform a single-handed fluid draw, many health workers use a two-step technique: they grasp the syringe with their first three fingers and use their little finger to initially retract the plunger a short distance, and they then reset their hand lower on the syringe barrel and use their little finger and perhaps also their ring finger to move the plunger further.

This two-step procedure is awkward. The pinky finger is not strong, especially when applying a lateral force. Resetting their hand on the syringe takes time. Further, resetting their hand often causes the needle to move within the patient, which can thereby cause pain or internal cuts or tears, increasing the likelihood that the patient thrashes. A better way to retract a plunger during a fluid draw is needed.

BRIEF DESCRIPTION OF THE DRAWINGS

Referring to the drawings.

DETAILED DESCRIPTION

Figure 1:
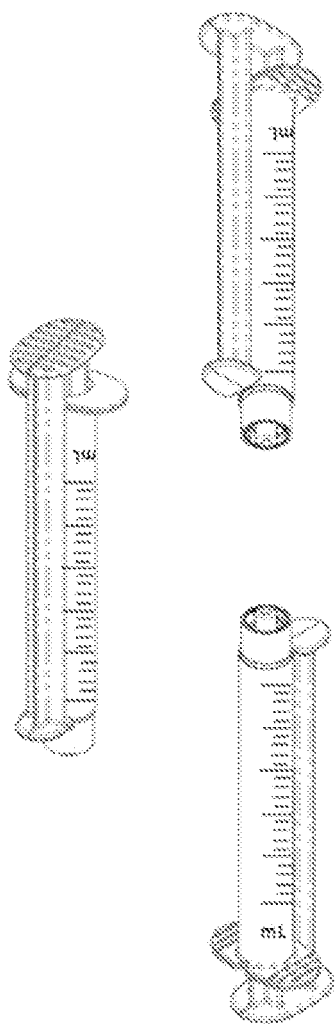
FIG. 1 is perspective views of three syringes with plunger extensions, showing the syringes in contracted conditions respectively.
Figure 2:
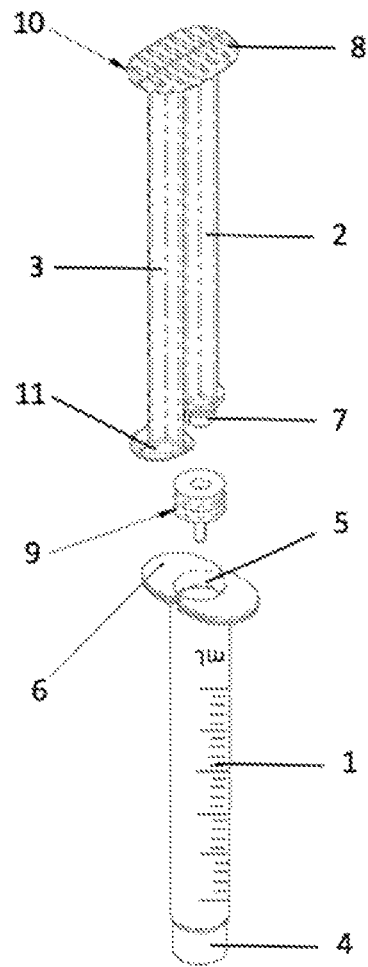
FIG. 2 is a perspective view illustrating all the pieces of the improved syringes with plunger extension.

Reference now is made to the drawings, in which the same reference characters are used throughout the different figures to designate the same elements. FIG. 1 is perspective views of three improved syringes with plunger extensions, useful for holding the syringe and retracting the plunger with only a single hand. Each of the syringes can be used, of course, in a similar fashion to a conventional syringe to give injections, to aspirate, and to perform other procedures in which the plunger is advanced into the barrel. These syringes, however, are unique because the plungers can be retracted easily with a single hand. Reference will be made to the syringe with plunger extension. FIG. 2 shows that the syringe with plunger extension includes a barrel (1), a plunger (2) fit to the barrel (1), and a plunger extension (3) integrated with the plunger (2).

The barrel (1) of the syringe with plunger extension is a preferably transparent or translucent cylindrical body, preferably having graduated volume indication lines arranged axially along the barrel (1). The barrel (1) has a tip (4) and an open bottom (5). The tip (4) is usually a coupling, such as a luer-type lock coupling, to which a needle, tubing, or other implement can be attached. In this embodiment, the tip (4) has an upstanding open post and a coaxial, upstanding outer sidewall formed with internally-directed helical threads.

The bottom (5) of the barrel (1) is open and receives the plunger (2) there through. At the bottom (5), the barrel (1) is formed with outwardly-extending flanges (6). The flanges (6) extend from the sidewall of the barrel (1) and allow a health worker to brace the syringe with plunger extension in his (her) fingers against the flanges (6). In the embodiments shown in FIG. 1 and FIG. 2, the flanges (6) extend outward diametrically from each other. In other embodiments, there are more or fewer flanges, and they have different sizes. For example, in some embodiments, a single, continuous flange extends entirely around the bottom (5), forming an annulus.

The plunger (2) is mounted for sliding, reciprocal movement within the barrel (1). The plunger (2) has a front (7), an opposed back (8), and a body extending there between. The front (7) of the plunger (2) is a piston (9) or seal, snug fit within the barrel (1) and securely mounted to the front (7) of the plunger (2). The piston (9) is constructed from a material or combination of materials having characteristics of inertness, low permeability, durability, and compressibility, such as isoprene, chlorobutyl, natural and synthetic rubber compounds, as well as thermoplastic elastomers. In some embodiments, the piston (9) is coated in silicone, polytetrafluoroethylene ("PTFE") or other similar coating to improve the sliding performance against friction between the piston (9) and the barrel (1). The piston (9) divides the interior of the barrel (1) into a reservoir and an open interior, with the reservoir extending between the piston (9) and the tip (4) of the barrel (1), and the open interior extending between the piston (9) and the bottom (5) of the barrel (1).

The body of the plunger (2) consists of four axially-extending ribs extending from an axial, central core. The ribs provide the plunger with rigidity and prevent the plunger (2) from bending within the barrel (1). The back (8) of the plunger (2) is integrated and formed with outwardly-extending flanges (8, 10). The flanges (8, 10) extend from the ribs and allow a health worker to draw the plunger (2) out of the barrel (1) with his fingers, by gripping the flanges (8, 10) and pulling. In the embodiments shown in FIG. 1 and FIG. 2, the flanges (8, 10) extend outward diametrically from each other. In other embodiments, there are more or fewer flanges, and they have different sizes. For example, in some embodiments, a single, continuous flange extends entirely around the back (8) of the plunger (2), forming an annulus.

The plunger extension (3) is formed integrally to one of the flanges of plunger (8) and extends to a front or head (11) proximate to the piston (9) and proximate to the tip (4) of the barrel (1) so that the health worker can grip the barrel (1) and depress the head (11) with a single hand, as will explained. The plunger extension (3) includes a head (11), a back (10), and a body there between. The head (11) is a generally flat pad or platform, oriented normal to the alignment of the body of the plunger extension (3), providing a spot to depress the plunger extension (3) with a digit such as a thumb. The head (11) is formed integrally and monolithically on the body of the plunger extension (3). The plunger extension (3) is designed just like the plunger described above except the flat head (11), it looks like two integrated plungers stay parallel together by the flanges (8, 10) from FIG. 2. Such plunger-shaped plunger extension (3) is structured in a unique design which is different from all the prior arts.

The body of the plunger extension (3) extends rearwardly to the flanges (8, 10). The body of the plunger extension (3) includes four ribs extending radially outward from an axial, central core. The ribs extend entirely from the head (11) to the back (10) and provide the body with rigidity to prevent the extension (3) from bending during depression. The body of the plunger extension (3) is oriented parallel to the plunger (2) and formed integrally to it. The body of the plunger extension (3) is preferably the same length as the body of the plunger (2), so that the head (11) and the piston (9) are approximately co-located with respect to the barrel (2). This allows the health worker to observe the position of either the piston (9) or the head (11) with respect to the indication lines of the barrel (1). In some embodiments, the body of the plunger extension (3) may be just shorter than the body of the plunger (2). This allows the health worker to observe the position of the piston (9) with respect to the indication lines of the barrel (1), with obstruction of a thumb placed on the head (11) of the plunger extension (3).

The back (10) of the plunger extension (3) is formed integrally and monolithically to the back (8) of the plunger (2) as a single, unitary piece. In the embodiment shown in FIG. 1 and FIG. 2, the back (10) of the plunger extension (3) is a monolithic tab or projection from one of the flanges (8, 10) of the plunger (2). In other embodiments, the back (10) of the plunger extension (3) is a monolithic tab or projection from between the flanges (8, 10). In yet other embodiments, the back (10) of the plunger extension (3) may be clipped, snapped, or otherwise fastened to the plunger (2) to securely fix the extension (3) to the plunger (2) so that depression of the plunger extension (3) will cause the plunger (2) to retract out of the barrel (1).

FIG. 1 illustrates the syringe with plunger extension in a contracted state, in which the reservoir has a zero volume. The plunger (2) is advanced within the barrel (1) and the head (11) of the extension (3) is proximate to the tip (4) of the barrel (1). When the syringe with plunger extension is in a retracted state, the reservoir has a maximum—or near maximum—volume. The plunger (2) is retracted within the barrel (1) and the head (11) of the plunger extension (3) is now proximate to the bottom (5) of the barrel (1). Depressing the head (11) of the plunger extension (3) moves the syringe from the contracted state of the FIG. 1 to the retracted state.

The syringe with plunger extension is useful to draw blood or fluid with a single hand, but also to give injections, aspirate, or perform other medical procedures. In FIGS. 1-2, the syringe with plunger extension is shown without a needle, but one having ordinary skill in the art will readily understand the below even without depiction of the needle. A needle would be fitted to the tip (4) of the syringe to ready the syringe with plunger extension for drawing fluid.

Once the syringe with plunger extension is ready, it is grasped by a single hand. Preferably the first two or three fingers (index, middle, and perhaps the ring finger) are wrapped around the barrel (1) between the tip (4) and the flanges (6). If there is room, the little finger may also be wrapped around the barrel (1); if there is not sufficient room, the little finger can rest just below the flanges (6). The syringe with plunger extension is oriented so that both the barrel (1) and the plunger extension (3) rest against the palm, with the extension (3) behind, or directed toward the health worker's arm and the barrel (1) directed away from the health worker's arm. The health worker places his thumb atop the head (11) of the plunger extension (3). In this condition, the health worker holds the syringe with plunger extension in a preferred grip.

Once the syringe with plunger extension is held in the preferred grip, the health worker can stick the patient with the syringe with plunger extension. The needle pierces the patient's skin and bodily tissues to a desired depth. When that depth is reached, and the tip of the needle is in the location from which bodily fluid is to be drawn, the health worker depresses the head (11) with his (her) thumb. The health worker pushes the head (11) back toward the bottom (5) of the barrel (1), thereby causing the plunger (2) to retract within the barrel (1) and the reservoir to enlarge in volume. Because the piston (9) is snug fit within the barrel (1), retraction of the plunger (2) creates a vacuum within the reservoir, causing the bodily fluid to flow into the reservoir. In other words, as the health worker depresses the head (11) of the plunger extension (3), the reservoir fills with bodily fluid.

The health worker draws the desired volume of bodily fluid and then stops depressing the head (11) of the plunger extension (3), observing the position of the piston (9) with respect to the indication lines marked on the barrel (1). Once the desired volume of fluid has been drawn, the health worker removes the spike from the patient; the draw procedure is complete.

The motion of depressing the head (11) of the extension to retract the plunger (2) is continuous and smooth, without interruption, and is accomplished without using a second hand. As described above, only the single hand is used, and the position of the hand and the fingers barely changes. The motion is quick, requiring approximately less than a second.

To operate the syringe with plunger extension in a conventional fashion, the reservoir is filled with a liquid, the syringe with plunger extension is taken up by hand, and the needle is pierced through the skin and body tissue of the patient. The health worker then advances the plunger (2) through the barrel (1) to empty the contents of the reservoir into the patient. The health worker may use one or two hands for this procedure.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

What is claimed is:

1. A single-hand controlled syringe with plunger extension comprising a barrel, a plunger with a piston at one end, and a plunger extension, wherein said plunger fits to said barrel; wherein said plunger extension is integrated with said plunger at ends of said plunger extension and said plunger; wherein said plunger extension is oriented parallel to said plunger and said barrel; wherein said barrel of the syringe with plunger extension is a transparent or translucent cylindrical body having graduated volume indication lines arranged axially along said barrel; wherein said barrel of the syringe with plunger extension has a tip and an open bottom; wherein said tip is a luer-type lock coupling, to which a needle, tubing, or other implement can be attached; wherein said tip has an upstanding open post and a coaxial, upstanding outer sidewall formed with internally-directed helical threads; wherein said open bottom of said barrel is open and receives said plunger there through; wherein there are outwardly-extending flanges formed with said open bottom of said barrel; wherein said plunger is mounted for sliding or reciprocal movement within said barrel; wherein said plunger consists of a front, a back, and a body extending there between; wherein said front of said plunger is securely mounted to said piston which snug fit within said barrel of said syringe; wherein said body of said plunger consists of four axially-extending ribs extending from an axial, central core; wherein said back of said plunger is integrated with said body of said plunger and is formed with outwardly-extending flanges; wherein said plunger extension is designed like said plunger; wherein said plunger extension consists of a head, a back, and a body there between; wherein said head of said plunger extension is close to said piston and close to said tip of said barrel; wherein said head of said plunger extension is a generally flat pad or platform and oriented normal to the alignment of said body of said plunger extension, providing a spot to depress said plunger extension with a thumb to move said syringe from a contracted state to a retracted state; wherein said head of said plunger extension is formed integrally and monolithically on said body of said plunger extension; wherein said back of said plunger extension is formed integrally and monolithically to said back of said plunger as a single, unitary piece; wherein said body of said plunger extension consists of four ribs extending radially outward from an axial, central core; wherein said ribs of said plunger extension extend entirely from said head to said back of said plunger extension and provide said body of said plunger extension with rigidity to prevent said plunger extension from bending during depression; wherein said body of said plunger extension is oriented parallel to said plunger and is the same length as or shorter than said body of said plunger; wherein said single-hand controlled syringe with plunger extension has only one said barrel.

\* \* \* \* \*